United States Patent
Fuertes Pena

(10) Patent No.: US 11,529,558 B2
(45) Date of Patent: Dec. 20, 2022

(54) WEARABLE GAMING DEVICE AND METHOD THEREOF

(71) Applicant: Boreal Technology & Investment S.L., Malaga (ES)

(72) Inventor: Jose Fuertes Pena, Malaga (ES)

(73) Assignee: BOREAL TECHNOLOGY & INVESTMENT S.L., Malaga (ES)

(*) Notice: Subject to any disclaimer, the term of this patent is extended or adjusted under 35 U.S.C. 154(b) by 255 days.

(21) Appl. No.: 16/903,743

(22) Filed: Jun. 17, 2020

(65) Prior Publication Data
US 2021/0154571 A1 May 27, 2021

(30) Foreign Application Priority Data

Nov. 4, 2019 (EP) .................................... 19382962

(51) Int. Cl.
*A63F 13/285* (2014.01)
*A61N 1/04* (2006.01)
(Continued)

(52) U.S. Cl.
CPC .......... *A63F 13/285* (2014.09); *A61N 1/0452* (2013.01); *A61N 1/0484* (2013.01);
(Continued)

(58) Field of Classification Search
CPC .. A63F 13/285; A63F 13/24; A63F 2300/302; A63F 13/50; A61N 1/0452;
(Continued)

(56) References Cited

U.S. PATENT DOCUMENTS 9,293,015 B2 * 3/2016 Mar ....................... G06F 3/016
2006/0217768 A1 * 9/2006 Buhlmann ......... A61N 1/36034
607/2
(Continued)

FOREIGN PATENT DOCUMENTS

EP 1533678 A1 5/2005
EP 2291115 B1 9/2013
(Continued)

OTHER PUBLICATIONS

European Search Report for Corresponding European Application No. 19382962.9 (7 Pages) (dated Jan. 28, 2020).

*Primary Examiner* — Thomas J Hong
*Assistant Examiner* — Carl V Larsen
(74) *Attorney, Agent, or Firm* — Lucas & Mercanti, LLP

(57) ABSTRACT

A gaming wearable device directed to be worn by a player whilst playing a videogame is provided. The gaming wearable device of the invention hereby disclosed allows the user to feel the sensations currently suffered by a character of a video game, in such a way a deeply immersive gaming experience is provided. The gaming wearable device is a vest or a suit where a series of electrodes have been strategically placed in such a way that every single muscle covered by the suit can be stimulated electrically by means of pulses generated by a control unit. The electrodes are covered with a conductive gel layer allowing a quick and easy fix on the skin of the gamer, providing a higher electrical conductivity as well.

7 Claims, 4 Drawing Sheets

(51) Int. Cl.
*A63F 13/24* (2014.01)
*G06F 3/01* (2006.01)
*A63F 13/50* (2014.01)

(52) U.S. Cl.
CPC .............. *A63F 13/24* (2014.09); *G06F 3/016* (2013.01); *A63F 13/50* (2014.09); *A63F 2300/302* (2013.01)

(58) Field of Classification Search
CPC ................ A61N 1/0484; A61N 1/0492; A61N 1/36034; G06F 3/016
See application file for complete search history.

(56) References Cited

U.S. PATENT DOCUMENTS

| | | | |
|---|---|---|---|
| 2011/0088925 A1* | 4/2011 | Tatsumi | H01B 7/06 174/69 |
| 2012/0144551 A1* | 6/2012 | Guldalian | A61N 1/0484 2/102 |
| 2013/0062095 A1* | 3/2013 | Huang | H01B 7/083 29/525.01 |
| 2014/0135593 A1* | 5/2014 | Jayalth | A61B 5/296 600/301 |
| 2015/0331488 A1* | 11/2015 | Grant | G06F 3/014 715/702 |
| 2018/0036531 A1 | 2/2018 | Schwarz et al. | |
| 2018/0043151 A1 | 2/2018 | Ejiri et al. | |
| 2018/0214692 A1 | 8/2018 | Esh et al. | |
| 2019/0217078 A1 | 7/2019 | Yang et al. | |
| 2019/0265796 A1* | 8/2019 | Levesque | G06F 3/016 |
| 2020/0086606 A1* | 3/2020 | Takahashi | C09J 9/02 |
| 2020/0107758 A1* | 4/2020 | Lenigk | A61B 5/002 |
| 2020/0221965 A1* | 7/2020 | Narusawa | A61B 5/27 |
| 2020/0237031 A1* | 7/2020 | Daniels | H04W 4/029 |
| 2020/0406119 A1* | 12/2020 | Woltermann | G11B 27/10 |
| 2021/0059605 A1* | 3/2021 | Myers | A61B 5/27 |
| 2022/0002915 A1* | 1/2022 | Chen | D03D 15/56 |

FOREIGN PATENT DOCUMENTS

| | | |
|---|---|---|
| EP | 3023867 A2 | 5/2016 |
| EP | 3182266 A1 | 6/2017 |
| JP | H11309219 A | 11/1999 |
| WO | 2015100482 A1 | 7/2015 |

* cited by examiner

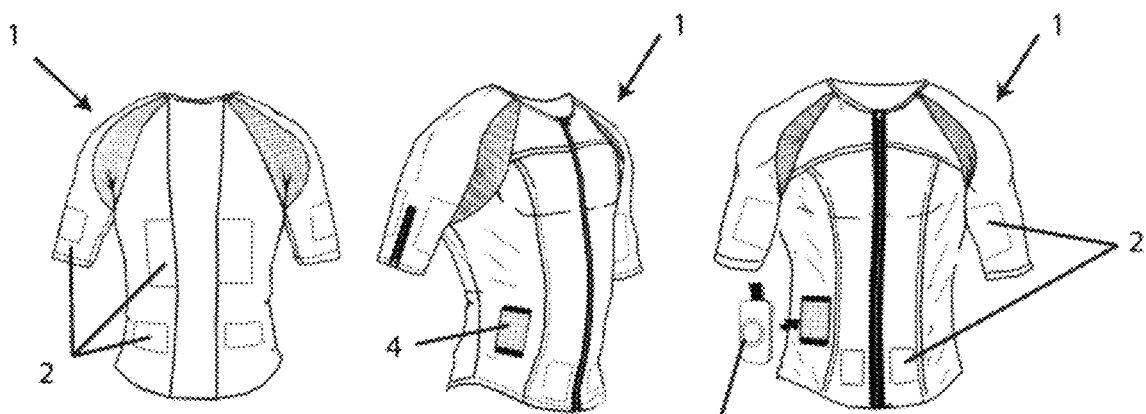
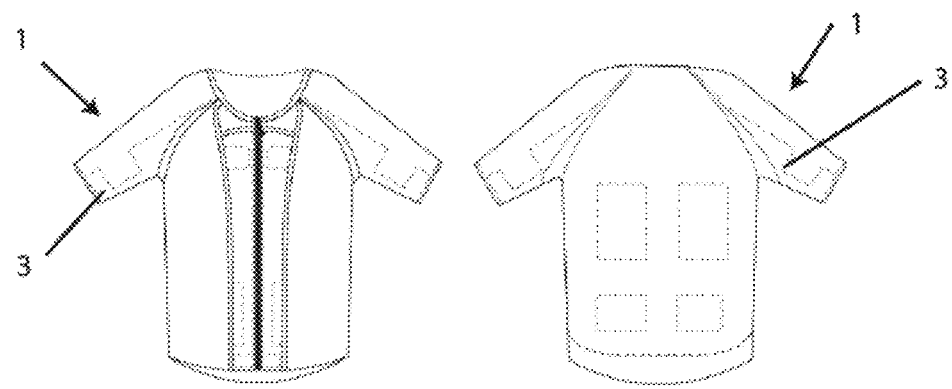

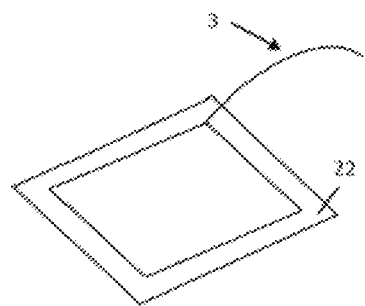
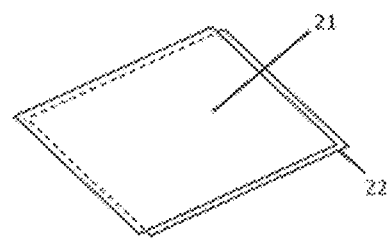
Figure 4.a   Figure 4.b
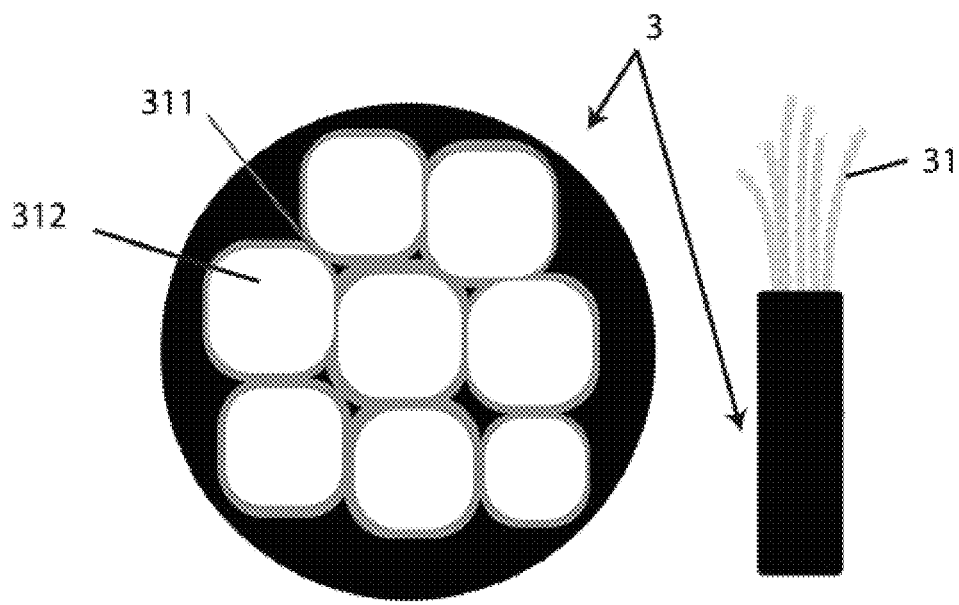
Figure 5

WEARABLE GAMING DEVICE AND METHOD THEREOF

CROSS REFERENCE TO RELATED APPLICATION

This application claims the benefit of priority of European Patent Application No. 19382962.9, filed on Nov. 4, 2019, which is incorporated herein by reference.

TECHNICAL FIELD

The invention relates to the technical field of wearable devices and more particularly to wearable gaming devices.

The object of the invention is directed to a wearable gaming device providing physical feedback to a user from an application, particularly a computer video game or other software applications.

BACKGROUND OF THE INVENTION

The world of video games has been surrounded by peripherals aimed for gaming since the very beginning. Joysticks were widely deployed in the 80s whereas haptic devices were becoming common during the 90s.

Haptic devices were, and still are, mainly based on mechanical based vibrating devices which generate a vibration by means of an electrically powered motor. These devices do not provide a real sensation or feeling of the situation currently being performed on the video game, since the haptic engine does stimulate the external part of the body only; hence any deeper action cannot be properly simulated, i.e. a stab in the stomach requires from a deeper perception rather than an external vibration or pulse on the abdominal area which can be either a punch or just low kick on the video game.

Hence, it was widely acknowledged that deeper sensations were meant to be provided for a real video game experience also applicable to any similar human-machine interaction.

In this sense, patent application EP3023867A2 discloses a method for interactive physiological and technological synchronization of a user with a virtual environment including taking the user's biometric and/or kinematic parameters, transferring the user's biometric and/or kinematic parameters to an application program, generating feedback signals in the application program, transmitting the feedback signals to a computing device, processing the feedback signals and supplying feedback pulses which invoke physical sensations in the nervous system of the user through contact with the user's skin, wherein the feedback pulses are supplied using electrical pulses. The method disclosed by EP3023867A2 requires a prior taking the user's biometric and/or kinematic parameters which are transferred to an application program.

EP2291115B1 discloses a wearable device and system for a tamper free electric stimulation of a body; this device is mainly oriented to an application of Electrical muscle stimulation (EMS), also known as neuromuscular electrical stimulation (NMES) or electromyostimulation of a user's body which fits a portion of the user's body and includes at least one electrode embedded in the wearable device transferring a stimulating current to the user's body. The device of EP2291115B1 provides a connection point as an intermediate connection between the at least one electrode and a control unit configured to generate the stimulating current. In EP2291115B1 a detector is configured to detect if a change in a physical relationship between the connection point and the at least one electrode exceeds a predetermined threshold value, thereby enabling detection of misuse and tampering with the device.

U.S. Pat. No. 9,293,015B2 discloses a haptic drive circuit for an electrical muscle stimulation electrode which has an input for receiving a haptic signal based on a haptic effect from a haptic effects' processor. The drive circuit of U.S. Pat. No. 9,293,015B2 contains logic for generating an electrical muscle stimulation current based on the haptic signal; so, an electrode in contact with a user's skin receives the electrical muscle stimulation current, causing a haptic effect by contraction and relaxation of muscles near the electrode.

EP3182266A1 is aimed to determine a haptic effect and transmit a haptic signal associated with the haptic effect. The system disclosed in EP3182266A1 may also comprise a multifunction haptic output device configured to receive the haptic signal and output the haptic effect; said multifunction haptic output device may, in turn, comprise a single haptic actuator.

SUMMARY OF THE INVENTION

The present invention discloses a wearable gaming device and a method for physically stimulating a user wearing said wearable device whilst playing a video game.

Thus, a first aspect of the present invention relates to a wearable device, preferably implemented on a piece of garment which is provided with a plurality of electrodes arranged so they can stimulate at least one muscle or groups of muscles in such a way they produce a sequence of electrically generated stimuli representing a certain sensation associated to an action being carried out whilst playing a video game.

The object of the method for generating sensations on a user, playing a videogame wearing the cited wearable gaming device, is mainly directed to simulating actions being carried out on a video game whilst the user is playing said video game by means of electrically stimulating one or more muscles of said user.

The method of the invention is carried out by means of the control unit generating a series of electrical pulses which are directed to the electrodes. Said sensations are created by a control unit which may be furnished with a double H bridge where the output channels are connected to.

The method of the invention provides any type of wave and even move away from the pre-established waves known in the art, being able to generate signals in need of being located within the known standards. That is, this feature allows us to deviate from the traditional waves, the control unit may generate biphasic quadrangular, preferably symmetric, waves producing pulse/s so the muscle can be stimulated without the need for repetitions within a wave, that is, by means of an asynchronous impulse train.

Thanks to the possibility of being able to stimulate two muscles at the same time, the invention can generate impulse trains in two muscles and simulate for example a bullet that enters the chest and exits the back with bleeding in both parts. For this we have created an asymmetric and multiform wave in each of the muscles where the pulses related to the sensation are received, and with different depth and time, being able to create a more real sensation by being able to stimulate two muscles at the same time.

It is worth noting that in any embodiment of whichever aspect of the present invention the word "conductor" and/or "conductive" is irrespectively used referring to physical properties related to electrical conductivity a.

DESCRIPTION OF THE DRAWINGS

To complement the description being made and in order to aid towards a better understanding of the characteristics of the invention, in accordance with a preferred example of practical embodiment thereof, a set of drawings is attached as an integral part of said description wherein, with illustrative and non-limiting character, the following has been represented:

FIGS. 1a-1e.—Show a series of views of the wearable gaming device of the invention from different perspectives, so the different parts of its configuration can be appreciated. FIG. 1a shows a back view of the wearable gaming device; FIG. 1b shows a side view thereof; FIG. 1c shows a front view thereof; FIG. 1d shows inside out view of front part thereof; and FIG. 1e shows inside out view of the back part thereof.

FIGS. 4a, 4b.—Show two diagrams of the electrode of the wearable gaming device object of the invention. FIG. 4a shows the electrically conductive layer and a loop generated with at least the conductive part of conductive elastic core of the cable contacting the electrically conductive layer; FIG. 4b the electrically conductive gel layer arranged on top of the electrically conductive layer.

FIG. 5.—Shows a pair of diagrams where the cable and a cross section therein are represented, showing the outer electrically insulating structure, and a conductive elastic core comprising in turn an elastic structure covered with the conductor layer.

DETAILED DESCRIPTION

Figure 2:
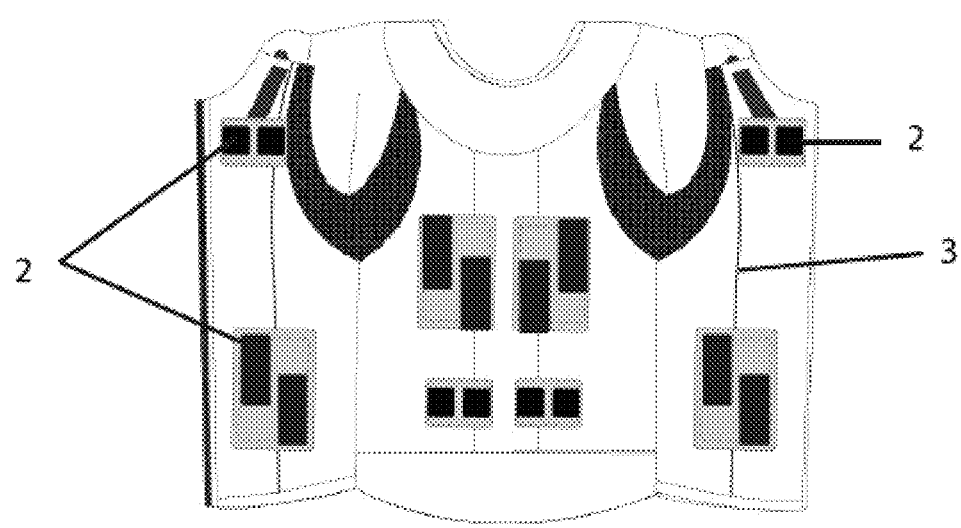
FIG. 2.—Shows a diagram of the wearable gaming device object of the invention as an open vest where all the parts are shown from the inside.

In a preferred embodiment of the object of one aspect of the invention, a wearable gaming devices (1) presented as a piece of garment is provided with set of electrodes (2) being connected by a cable (3) to a control unit (4) is presented; all of these, rendering a wearable gaming device (1) as the one depicted on FIGS. 1a-1e, where the cable (3) is depicted as being fastened, preferably by sewing, to the piece of garment such as the vest of FIG. 2.

Figure 3:
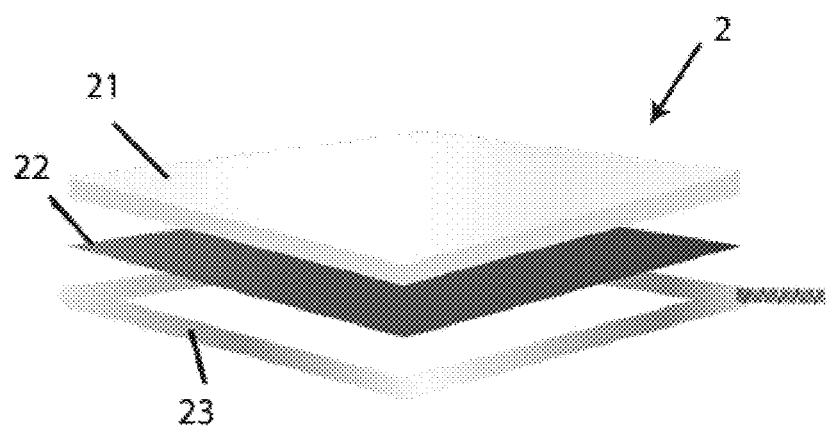
FIG. 3.—Shows an exploded view of the electrode showing the different layers thereof.

The cable (3) comprises an outer electrically insulating structure (33), and a conductive elastic core (31) comprising in turn an elastic structure (312) covered with an electrical conductor layer (311) configured to be electrically connected to a conductive layer (22) of the electrode (2), which is covered by an electrical conductive gel layer (21) which is a part of the electrode (2) as shown on FIG. 3. The electrical conductive gel layer (21) comprises an electrical conductive viscous gel allowing an easy and secure placement on the skin of the user, not requiring from water or any moist since it is made of an electrical conductor material in the form of a gel, further providing a lower electrical resistance for the body of the user. In a preferred embodiment of the invention a low viscosity conductive gel performed best overall having a relatively low magnitude of contact impedance and superior performance; being the conductive layer (22) of the electrode (2) made of a carbon-based material.

The core of the cable (3), referred as elastic cable (3) and depicted on FIG. 5, comprises a series of elastic structures (312), which can be made of elastomer filaments capable of stretching 160% of its length at rest, covered with enamelled copper wire thus defining the electrical conductor layer (311), preferably arranged in the form of zigzag to allow it to be stretched in conjunction with the elastomers so that the user has extreme comfort at the same time that the quality of the electrical signal sent does not suffer losses during the way to go through the wearable game device (1), in a preferred embodiment of the invention an elastic cable (3) with the following specification is preferred:

18.86% Elastomer
47.44% Enamelled copper wire.
33.70% Black textured polyamide thread.
Elasticity: 160%
Footage: 606 meters/kg The conductive elastic core (31) is covered by the outer electrically insulating structure (33), which may comprise textured polyamide wire/s and provides the structural function and to which an insulating additive might added so that it does not allow the transmission of electric current.

This cable (3) structure, comprising the outer electrically insulating structure (33), and conductive elastic fibres (31) comprising in turn an elastic structure (312) covered with a conductor layer (311) connecting to the conductive layer (22) of the electrode (2), allows that there is no leakage of electric current. Besides, and thanks to its elasticity, it adapts to the body once stitched to the piece of garment, preferably by means of an embroidery machine; hence, once the cable is fixed to the piece of garment, it always remains placed at a fixed position relative to the piece of garment, but at the same time, the already discussed cable (3) structure provides the required elasticity consistent with that of the material that makes up the piece of garment, i.e. Lycra®. The elastic cable (3) runs through the structure of the piece of garment from a connection of the control unit (4) to each of the electrodes (2) of the wearable gaming device, preferably twenty electrodes (2) having a cable (3) for each of the electrodes (2), in a preferred embodiment the cable (3) is attached to the control unit (4) by means of a magnetic pin—not represented in the figures—of the control unit (4). By means of an embroidery machine the cable (3) is inserted through each of the paths defined inside the piece of garment so that the connection between the magnetic input of the control unit (4) and the electrodes (2) sewn to the jacket can be fully connected. The connection of the cable (3) to the electrically conductive layer (22) made of conductive black carbon, will preferably occur by electrical contact of at last the conductor layer (311) of the cable (3) along the perimeter of said electrically conductive layer (22); hence the end of the cable (3) is properly prepared so that it provides 100% of conductivity.

In a preferred embodiment of the earlier introduced method of the invention and as a way of exemplifying the invention, the user playing a video game has a corresponding game character being shot at close range on the chest, for this to be achieved, the method of the invention envisages by means of the control unit (4) a set of sensations associated with a point-blank shot on the chest where a bullet enters the chest, coming out from the back.

In order to provide such a sensation, the wearable gaming device (1) comprising the piece of garment, the electrode (2) connected by a cable (3) to a control unit (4), is worn by the user playing a video game in such a way that, said electrode (2) being arranged at the piece of garment, stimulates at least one muscle of said user wearing the piece of garment related to those being involved in the sensation—namely chest and back muscles—when being shot as described; in order to do so the control unit (4) comprises information of each electrode (2) said information encompassing its position and the relative position of the electrode (2) with respect of the body of user, therefore to which muscle or muscles affects each electrode (2) or groups of electrodes (2) being configured to generate an electrical pulse commanded by the control unit (4) in response to an action occurring at the videogame play. Since the electrical conductive layer (22) of the electrode is arranged beneath the electrical conductive gel layer (21) of the electrode (2) as shown in FIG. 4b, the conductive gel layer (21) is fixed to the skin of the user due to the viscosity of the gel therefore providing a water-free fix and a better conductivity; thus, being the electrical conductive layer (22) in electrical contact with the conductor layer (311) of the cable (3) as per FIG. 4a, that is in turn embroidered to the garment allowing a free movement due to its elasticity, once the control unit (4) generates a pulse or group of pulses, said pulse is transmitted through the cable (3)—more precisely through the conductive elastic fibres (31) comprising an elastic structure (312) covered with a conductor layer (311)—reaching the muscle associated to the position of the electrode (2) is stimulated in an specific way signifying the sensation respectively produced by the action occurring to a respective character during the videogame play.

Thus, in the current scenario related to the explanatory embodiment of the method of the second aspect of the invention where the user is playing a FPS videogame where a bullet is shot and the character is hit on the chest, the bullet entering the chest and coming out from the back.

Figure 6:
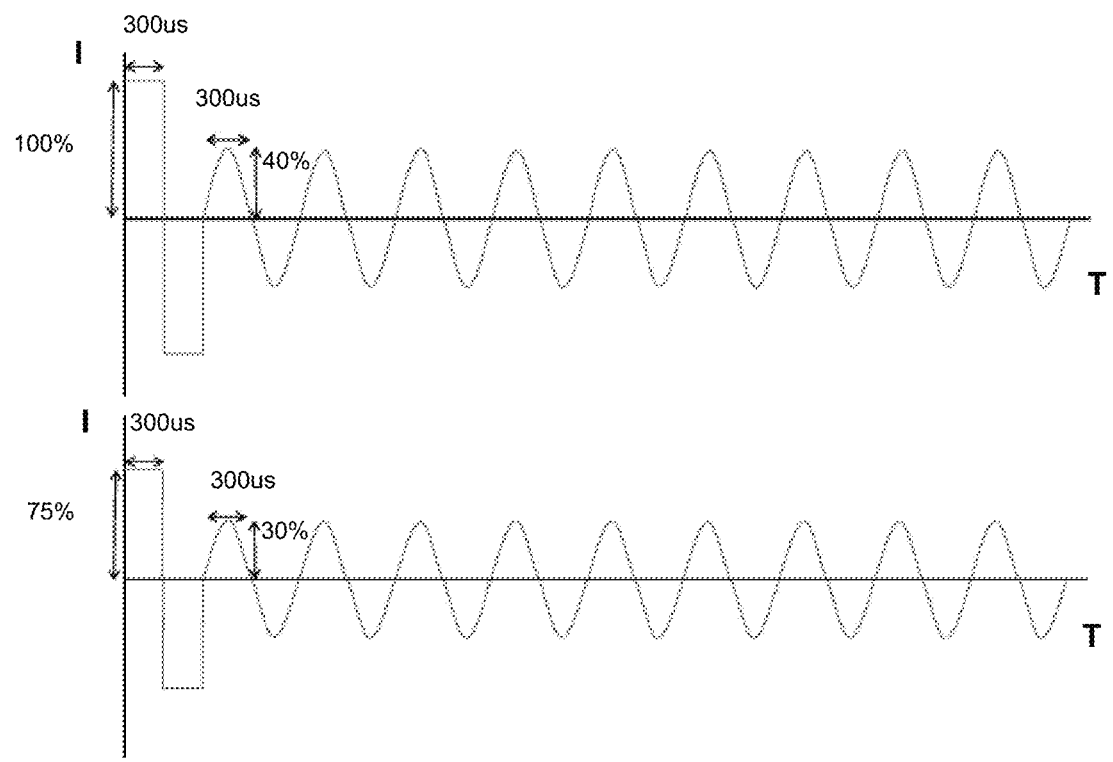
FIG. 6.—Shows two graphs where the waves generated by the control unit are represented.
Figure 7:
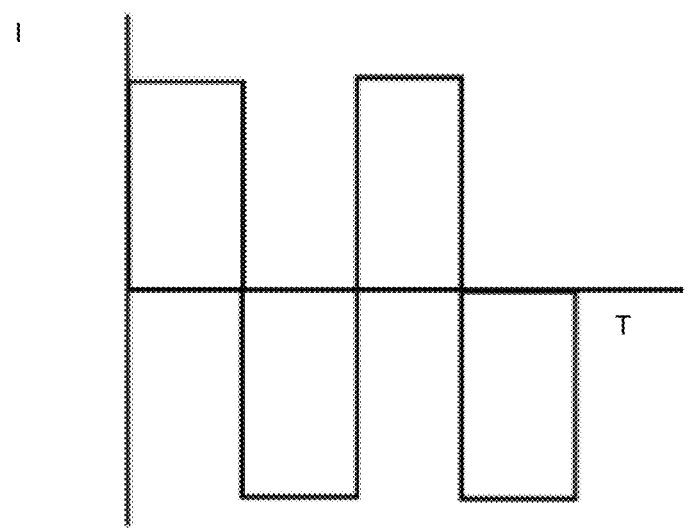
FIG. 7.—Shows a detail of the biphasic quadrangular and preferably symmetric waves that can be generated by the control unit.

In a yet preferred embodiment, the control unit (4) of the wearable gaming device (1) comprises a processing unit being capable of generating different types of wave like the ones depicted on FIG. 6 and/or FIG. 7, being biphasic quadrangular, and preferably symmetric, waves that can be generated by the control unit (4). In a preferred embodiment of the invention the control unit (4) may be furnished with at least two H shaped bridges respectively associated with five output channels, with the purpose of generating pulse/s which can be sent as stimuli to two or more muscles at the same time, making the sensations perceived by the player as real as possible. As the skilled person would acknowledge, this can be achived because the object of the invention yields a type of wave that does not require from adapting to a preestablished frequency type of wave (periodicity). The number of channels and bridges can be modified whilst keeping the symmetry of the output channels.

The variables used to create the sensations are grouped as tracks; being a train a set of tracks previously designed and resulting in a respective sensation; each track comprises one or more pulses, preferably with identical wave characteristics that, properly ordered, form the pulse train. Those related for a bullet that impacts the right pectoral muscle and leaves the right dorsal muscle (leaving a brief bleeding sensation) may be listed as follows:

Track 1 (input impact):
　Channel Number: 5 (right pectoral muscle)
　TIP: positive pulse time: 300 us
　TIN: 300 us negative pulse time
　TP: 0 ds
　TPC: 200 us
　I (Intensity): 100%
　No. Cycles: 1
　Obligation (S/N): S
Track 2 (output impact):
　Channel Number: 1 (right dorsal muscle)
　TIP: positive pulse time: 300 us
　TIN: 300 us negative pulse time
　TP: 0 ds
　TPC: 0 ds
　I (Intensity): 75%
　No. Cycles: 1
　Obligation (S/N): S
Track 3 (input bleeding):
　Channel Number: 5 (right pectoral muscle)
　TIP: positive pulse time: 300 us
　TIN: 300 us negative pulse time
　TP: 0 us
　TPC: 500 us
　I (Intensity): 40%
　No. Cycles: 500
　Obligation (S/N): N
Track 4 (bleeding at the start):
　Channel Number: 1 (right dorsal muscle)
　TIP: positive pulse time: 300 us
　TIN: 300 us negative pulse time
　TP: 0 us
　TPC: 500 us
　I (Intensity): 30%
　No. Cycles: 500
　Obligation (S/N): N Being
Channel Number: number of the output channel
TIP: positive pulse time 150 us-400 us each
TIN: negative pulse time 150 us-400 us each
TP: pause time between channels
TPC: pause time between cycles.
I: Intensity (mA).
No. Cycles: Number of cycles
Obligation (S/N).

In this case, the sensation would be composed of: Track 1+Track 2+Track 3+Track 4, where track 1 and track 2 are sent at the same time and track 3 and track 4 are sent at the same time.

The invention claimed is:

1. A wearable gaming device comprising:
a piece of garment, at least one electrode connected by a cable to a control unit, said electrode being arranged at the piece of garment in such a way that at least one muscle of a user wearing the piece of garment is stimulated when the electrode generates an electrical pulse commanded by the control unit,
the electrode comprising an electrically conductive layer made of conductive material, and an electrically conductive gel layer arranged on top of the electrically conductive layer, and
the cable being embroidered to the garment and comprising an outer electrically insulating structure, and conductive elastic fibres comprising in turn an elastic structure covered with a conductor layer in electrical contact with the electrically conductive layer of the electrode,
wherein the conductor layer is made of enamelled copper wire arranged in zigzag to allow it to be stretched in conjunction with the elastic structure.

2. The wearable gaming device of claim 1, wherein the elastic structure comprises elastomer filaments capable of stretching 160% in length.

3. The wearable gaming device of claim 1, wherein the electrodes are arranged in pairs.

4. The wearable gaming device of claim 1, wherein the control unit comprises at least two H shaped bridges with respective groups of output channels where the cables are connected to.

5. The wearable gaming device of claim 4, wherein the control unit comprises at least two H shaped bridges with two groups of five channels.

6. A method for generating sensations on a user playing a videogame wearing a wearable gaming device comprising:
- a piece of garment, and
- at least one electrode connected by a cable to a control unit, said electrode being arranged at the piece of garment in such a way that at least one muscle of a user wearing the piece of garment is stimulated when the electrode generates an electrical pulse commanded by the control unit, wherein the electrode comprises:
  - an electrically conductive layer made of conductive material, and
  - an electrically conductive gel layer arranged on top of the electrically conductive layer, and
- the cable being embroidered to the garment and comprising an outer electrically insulating structure, and conductive elastic fibres comprising in turn an elastic structure covered with a conductor layer in electrical contact with the electrically conductive layer of the electrode,
- the method comprising the control unit generating at least one pulse to be sent to at least one of the electrodes by means of the cable connecting the control unit and the least one electrode, wherein the at least one pulse is generated by non-biphasic quadrangular waves.

7. The method of claim 6, wherein the control unit is furnished with a double H bridge where the output channels are connected to.

* * * * *